United States Patent [19]

Kugler et al.

[11] Patent Number: 5,071,813

[45] Date of Patent: Dec. 10, 1991

[54] ETA PHASE MATERIALS, METHODS OF PRODUCING THE SAME, AND USE THEREOF AS CATALYSTS FOR ALCOHOL SYNTHESIS, HYDROCARBON SYNTHESIS, HYDROCARBON HYDROGENATION AND HYDROCARBON CONVERSION REACTIONS

[75] Inventors: Edwin L. Kugler, Sykesville, Md.; Larry E. McCandlish, Highland Park; Allan J. Jacobson, Princeton; Russell R. Chianelli, Somerville, all of N.J.

[73] Assignee: Exxon Research and Engineering Company, Florham Park, N.J.

[21] Appl. No.: 513,344

[22] Filed: Apr. 20, 1990

Related U.S. Application Data

[63] Continuation-in-part of Ser. No. 336,998, Apr. 12, 1989, abandoned, which is a continuation-in-part of Ser. No. 197,356, May 23, 1988, abandoned.

[51] Int. Cl.$^5$ ............................................. B01J 27/22
[52] U.S. Cl. .................................... 502/177; 502/200; 502/439; 423/364; 423/367; 423/371; 423/409; 423/439
[58] Field of Search ...................... 502/177, 280, 439; 423/364, 367, 371, 439, 409

[56] References Cited

U.S. PATENT DOCUMENTS

| | | | |
|---|---|---|---|
| 3,757,878 | 9/1973 | Wilder | 175/409 |
| 4,522,708 | 6/1985 | Leclerq et al. | 502/177 |
| 4,559,316 | 12/1985 | Mazanec et al. | 502/177 |
| 4,595,672 | 6/1986 | Ho et al. | 502/219 |
| 4,663,023 | 5/1987 | McCandish et al. | 208/112 |
| 4,664,899 | 5/1987 | Kimmel et al. | 423/439 |
| 4,703,028 | 10/1987 | Steininger | 502/177 |
| 4,705,619 | 11/1987 | McCandish et al. | 208/112 |
| 4,752,456 | 6/1988 | Yoda et al. | 423/439 |

OTHER PUBLICATIONS

Chem. Abstract 73:92208g.

Primary Examiner—Anthony McFarlane
Attorney, Agent, or Firm—S. Persley; J. Simon

[57] ABSTRACT

An eta phase composition in powder form, prepared in the absence of sulfur or sulfur bearing compounds, having a surface area greater than about 2m$^2$/g and consisting of $X_6Y_6Z_a$ wherein X is at least one element selected from the group consisting of Mo and W, Y is at least one element selected from the group consisting of Fe, Co, Ni, Mo and W, Z is at least one element selected from the group consisting of C, N and combinations thereof such that when Z is N, a is greater than or equal to 1 but less than or equal to 2 and when Z is C, a is greater than 1 but less than or equal to 2 except when Z is C and Y is Fe, then a is greater than or equal to 1 but less than or equal to 2. The eta phase may be a carbide, nitride or carbonitride. A method for producing the eta-phase composition includes providing a precursor compound including at least two eta-phase forming metals, and a ligand containing carbon, nitrogen or combinations thereof. The precursor compound is thermally decomposed in a nonoxidizing atmosphere, free of sulfur or sulfur bearing compounds, and reacts with carbon or nitrogen derived from the decomposition of the ligand with the metals to form the eta-phase. The eta phase forming metals are at least two of the metals tungsten, molybdenum, nickel, cobalt and iron. These eta-phase composition may be used for producing or converting hydrocarbons or alchols. This includes hydrogenation of CO (to produce at least one hydrocarbon or at least one alcohol and hydrogenation of unsaturated hydrocarbons, aromatic hydrocarbons and olefinic hydrocarbons), isomerization and dehydrogenation.

13 Claims, No Drawings

ETA PHASE MATERIALS, METHODS OF PRODUCING THE SAME, AND USE THEREOF AS CATALYSTS FOR ALCOHOL SYNTHESIS, HYDROCARBON SYNTHESIS, HYDROCARBON HYDROGENATION AND HYDROCARBON CONVERSION REACTIONS

This a continuation-in-part of U.S. Ser. No. 336,998 filed Apr. 12, 1989, now abandoned, which is a continuation-in-part of U.S. Ser. No. 197,356 filed May 23, 1988, now abandoned, which is based on Information and Belief.

FIELD OF THE INVENTION

This invention relates to powder of an eta-phase structure having an increased surface area and to a method for using the same in producing or converting hydrocarbons.

BACKGROUND OF THE INVENTION

Eta-phase structures, such as eta-phase carbides, nitrides and carbonitrides are known in the art for use as hardening dispersions in a metal or alloy matrix. Eta-phase materials are conventionally produced by heating metals with a source of carbon or nitrogen. This may be achieved, for example, by vacuum arc melting. Eta-phases can be present in steels containing, for example, nickel and molybdenum and may be formed in situ during thermal processing of these steels. These eta-phases may be crushed and milled to a desired particle size distribution. Typically, this thermal processing involves heating in the presence of sulfur or sulfur bearing compounds. For example, U.S. Pat. No. 4,595,672, Ho et al, teaches a method of producing self-promoted molybdenum sulfide and tungsten sulfide hydrotreating catalysts. The method involves heating one or more molybdate and/or tungstate catalyst precursors of the general formula $ML(Mo_yW_{1-y}O_4)$, where M is one or more divalent promoter metals selected from Mn, Fe, Co, Ni, Cu, Zn, and mixtures thereof and L is one or more, neutral, nitrogen-containing ligands, at least one or more of which is a chelating ligand polydentate ligand. The heating is conducted in a non-oxidizing atmosphere and in the presence of sulfur or sulfur bearing compounds, such as $H_2S$. Sulfur reacts with these catalyst precursors to form sulfided materials.

P. Ettmayer and R. Suchentrunk, "Thermal Stability of n-Carbides", Monatsh. Chem., Vol. 101(4), p. 1098-1103 (1970) also printed in Chem. Abstracts, Equilibriums and Solutions, Vol. 73, p. 313, reference article 92208g, 1970 Edition, disclose the formation of eta-phase carbides having the general formula $n-M_6M^1_6C$ where M is Fe, Co or Ni and where $M^1$ is Mo or W. Eta-phase carbides covered in this article include: $Fe_6W_6C$, $Co_6Mo_6C$, $Co_6W_6C$, $Ni_6Mo_6C$ and $Ni_6W_6C$. However, the stoichiometry of these eta-phase carbides employ a single carbon atom and only a single metal from groups M and $M^1$. Moreover, the formation of $Fe_6Mo_6C$ eta-phase carbides was not observed.

Conventional eta-phase structures have low surface area and are difficult to synthesize Therefore, they have not been known or considered for use as catalysts Also, conventional methods for making eta-phase structures do not produce high surface area eta-phase materials and are not formulated in a non-oxidizing atmosphere free of sulfur or sulfur bearing compounds.

It is accordingly a primary object of the present invention to provide an eta-phase structure in powder form and a method for using the same as a catalyst in converting or producing hydrocarbons in a more efficient manner, particularly from the cost standpoint, than catalysts conventionally used for this purpose.

A more specific object of the invention is to provide a method for producing a high surface area eta-phase powder for use as a catalyst wherein a precursor salt compound is thermally decomposed in a non-oxidizing atmosphere free of sulfur or sulfur bearing compounds to react with carbon, nitrogen or combinations thereof, at an elevated temperature and pressure.

Another object of the invention is to provide eta-phase powder for use as a catalyst effective for hydrocarbon or alcohol production or conversion that provides results similar to those achieved with more expensive noble metals, such as platinum and palladium, conventionally used for this purpose.

Additional objects and advantages of this invention are set forth in the description and examples that follow. Other objectives falling within the scope of the invention will be obvious from the description or may be learned by the practice of the invention. The objects and advantages of the invention may be realized and obtained by the compositions and methods particularly set forth herein.

SUMMARY OF THE INVENTION

In accordance with the invention, the composition thereof comprises an eta-phase in powder form, prepared in the absence of sulfur or sulfur bearing compounds. The powder has a surface area greater than 2 meters$^2$/gram (m$^2$/g). The eta-phase is a eta-phase carbide, eta-phase nitride or eta-phase carbonitride, present either singly or in combination. The eta-phase material has a composition of the general formula $X_6Y_6Z_a$ wherein X is at least one element selected from the group consisting of Mo (molybdenum) and W (tungsten), Y is at least one element selected from the group consisting of Fe (iron), Co (cobalt), Ni (nickel), Mo (molybdenum) and W (tungsten), Z is at least one element selected from the group consisting of C (carbon), N (nitrogen) and combinations thereof, and a is such that when Z is N, a is greater than or equal to 1 but less than or equal to 2 and when Z is C, a is greater than 1 but less than or equal to 2 except when Z is C and Y is Fe, then a is greater than or equal to 1 but less than or equal to 2.

Specifically, the eta phase materials in accordance with the invention may be:
$Mo_6Fe_6Z_a$, $Mo_6Co_6Z_a$, $Mo_6Ni_6Z_a$,
$Mo_6(FeCo)_6Z_a$, $Mo_6(FeNi)_6Z_a$, $Mo_6(CoNi)_6Z_a$,
$Mo_6(FeCoNi)_6Z_a$, $W_6Fe_6Z_a$, $W_6Co_6Z_a$,
$W_6Ni_6Z_a$, $W_6(FeCo)_6Z_a$, $W_6(FeNi)_6Z_a$,
$W_6(Co,Ni)_6Z_a$, $W(Fe,Co,Ni)_6Z_a$, $(W,Mo)_6Fe_6Z_a$,
$(W,Mo)_6Co_6Z_a$, $(W,Mo)_6Ni_6Z_a$,
$(W,Mo)_6(Fe,Co)_6Z_a$,
$(W,Mo)_6(Fe,Ni)_6Z_a$, $(W,Mo)_6(Co,Ni)_6Z_a$,
$(W,Mo)_6(Fe,Co,Ni)_6Z_a$,
wherein Z is at least one element selected from the group consisting of C, N and combinations thereof, and a is such that when Z is N, a is greater than or equal to 1 but less than or equal to 2 and when Z is C, a is greater than 1 but less than or equal to 2 except when Z is C and Y is Fe, then a is greater than or equal to 1 but less than or equal to 2.

Further in accordance with the invention, a method is provided for producing eta phase compositions. The method includes providing a precursor compound that includes at least two eta phase forming metals and a ligand containing carbon, nitrogen or combinations thereof. The precursor compound is thermally decomposed in a nonoxidizing atmosphere that is free of sulfur or sulfur bearing compounds, and reacts carbon, nitrogen or combinations thereof derived from the decomposition of the ligand with the metals of the precursor compound to form the eta phase. The eta phase forming metals may be tungsten, molybdenum, nickel, cobalt and iron, with preferred combinations thereof being molybdenum and nickel, molybdenum and cobalt, molybdenum and iron, tungsten and nickel, tungsten and cobalt, and tungsten and iron. The conditions for thermal decomposition of the ligand will vary depending upon the precursor compound including the ligand thereof. The temperature must be sufficiently high to remove the ligand from the metals and decompose the ligand, at least in part, to provide the required carbon and/or nitrogen necessary to react with the metals of the precursor compound. However, the temperature is not so high as to reduce the surface area of the final eta phase powder to 2 meters$^2$/gram or less. This temperature will also be dependent upon the reactor size, reactor geometry, the amount of precursor and so forth. This may be readily determined by routine experimentation as demonstrated by the specific examples herein.

The invention is also a method for producing or converting hydrocarbons and alcohols, including hydrogenation reactions using these eta-phase materials. The method comprises contacting a fluid, carbon-containing feedstock with a catalyst of an eta-phase composition in accordance with the invention as set forth above. This takes place in a reducing atmosphere at an elevated temperature and pressure effective for the desired hydrocarbon or alcohol production or conversion. In this regard, with respect to hydrogenation reactions, such may include the hydrogenation of CO to produce a hydrocarbon or an alcohol. Hydrogenation may be of unsaturated hydrocarbons, such as aromatic hydrocarbons and olefinic hydrocarbons. Hydrocarbon conversion reactions may be isomerization or dehydrogenation. The method for producing or converting hydrocarbons in accordance with the invention may include the specific eta phase listed above in accordance with the invention used as catalysts.

DETAILED DESCRIPTION OF THE PREFERRED EMBODIMENTS

Reference will now be made in detail to presently preferred embodiments of the invention, specific examples of which are described below.

The eta phase compositions in accordance with the invention are produced for example by the reduction decomposition of a suitable mixed metal coordination compound or mixed metal organometallic precursor at a temperature sufficient to yield an atomically mixed high surface area reactive product. The reduction is carried out in a non-oxidizing atmosphere free of sulfur or sulfur bearing compounds.

A specific, typical reaction employing a catalyst in accordance with the eta-phase compositions of the invention in a hydrogenation reaction wherein hydrogen and carbon monoxide are reacted at a suitable elevated temperature and pressure with a catalyst of the invention to produce a hydrocarbon and alcohol would be as follows: $H_2 + CO \; C_nH_{2n+2} + C_nH_{2n+1}OH$.

Specific examples demonstrating the effectiveness of Applicants' eta phase composition and method employing the same in producing hydrocarbons and alcohols or converting hydrocarbons are set forth hereinafter.

EXAMPLE 1

$Ni(en)_3MoO_4$ Catalyst Precursor Preparation

A tris(ethylenediamine) nickel molybdate, $Ni(en)_3MoO_4$, catalyst precursor was prepared by dissolving ammonium molybdate into ethylenediamine (en) and the resulting solution cooled to 0° C. in an ice bath. An aqueous solution of nickel chloride was slowly added, in aliquots, to the above solution, with agitation after the addition of each aliquot. A precipitate was formed and recovered by vacuum filtration. This precipitate was $Ni(en)_3MoO_4$ which was washed with water and acetone and then dried in a vacuum oven at 50° C. More specifically, 20.5 g of ammonium heptamolybdate, $(NH_4)_6Mo_7O_{24}\cdot4H_2O$, was added to 500 ml of ethylenediamine, $NH_2CH_2CH_2NH_2$, in a 1000 ml Erlenmeyer flask. The amount of ethylenediamine was greatly in excess of the stochiometric amount required to form the precursor compound and aids in its precipitation. In a separate flask 27 g of nickel chloride, $NiCl_2\cdot6H_2O$, were dissolved into 300 ml of distilled water. This $Ni^{2+}$ was added slowly, in aliquots, to the molybdate solution with agitation after each addition. The precipitate, $Ni(en)_3MoO_4$, which formed immediately, was collected on a Buchner funnel, washed with a small amount of water and then acetone. It was dried in a vacuum oven for 16 hours. 46 g of $Ni(en)_3MoO_4$ were recovered.

EXAMPLE 2

$Co(en)_3MoO_4$ and $Fe(en)_3MoO_4$ Preparation

The method of Example 1 was used with the substitution of either $CoCl_2\cdot6H_2O$ or $FeCl_2\cdot4H_2O$ for the $NiCl_2\cdot6H_2O$. In the synthesis of $Fe(en)_3MoO_4$ the solutions and the precipitate were handled under an inert blanket of nitrogen gas to prevent the oxidation of $Fe^{2+}$ to $Fe^{3+}$.

EXAMPLE 3

Preparation of $[Fe(en)_3]_{0.5}[Ni(en)_3]_{0.5}MoO_4$, $[Fe(en)_3]_{0.5}[Co(en)_3]_{0.5}MoO_4$, $[Co(en)_3]_{0.5}[Ni(en)_3]_{0.5}MoO_4$, etc.

The methods of Example 1 and Example 2 were used with equimolar mixtures of aqueous $Fe^{2+}$ and $Ni^{2+}$, $Fe^{2+}$ and $Co^{2+}$, and $Co^{2+}$ and $Ni^{2+}$ substituted respectively for the $Ni^{2+}$ aqueous solution used in Example 1. Again a nitrogen gas blanket was used where necessary to prevent the oxidation of these ions.

EXAMPLE 4

Preparation of $[M(en)_3]_{1-x}[M'(en)_3]_xMoO_4$ where both M and M' = Fe, Co, Ni The methods of Example 1 and Example 2 were used with mixtures of aqueous $M^{2+}$ and $M'^{2+}$ in the molar ratio $(1-x):x$, where x is greater than or equal to zero less than or equal to 1, substituted for the $Ni^{2+}$ aqueous solution of Example 1. A nitrogen gas blanket was used as in the previous examples.

EXAMPLE 5

Preparation of Ni(en)$_3$WO$_4$ 14.5 grams of tungstric acid, $H_2WO_4$, were dissolved in 150 ml of a 1:1 mixture of concentrated NH$_4$OH and water, and 150 ml of ethylenediamine. A clear solution was obtained by heating and stirring. In a separate vessel, 13.5 grams of NiCl$_2$.6H$_2$O was dissolved in distilled water and added to the hot tungstric acid solution. A precipitate, Ni(en)$_3$WO$_4$, formed as the volume of the mixture was reduced 50% by evaporating the solution. After cooling the mixture to room temperature, the product was collected by filtration on a Buchner funnel, washed with acetone, and dried.

EXAMPLE 6

Preparation of Co(en)$_3$WO$_4$ and Fe(en)$_3$WO$_4$

The method of Example 5 was used with the substitution of CoCl$_2$.6H$_2$O or FeCl$_2$.4H$_2$O for NiCl$_2$O.6$_{H2}$O. In the synthesis of Fe(en)$_3$WO$_4$ the procedure is carried out under an inert atmosphere to prevent the oxidation of $Fe^{2+}$ to $Fe^{3+}$.

EXAMPLE 7

Preparation of $[M(en)_3]_{1-x}[M'(en)_3]_x WO_4$ where both M and M'=Fe, Co, Ni The methods of Example 5 and Example 6 were used with mixtures of aqueous $M^{2+}$ and $M'^{2+}$ in the molar ratio (1−x):x, where x is defined as in Example 4, substituted for the $Ni^{2+}$ aqueous solution of Example 5.

EXAMPLE 8

Thermodynamically Controlled Preparation of Molybdenum Carbide Eta Phases

The reactive precursors were prepared in identical manners from the appropriate M'(en)$_3$MoO$_4$ salt and were synthesized by the methods of Examples 1 and 2, where M' is Ni, Co and Fe. The transition metal coordination compound was placed in a quartz boat in a 1.5" I.D. quartz tubular furnace and heated in a flowing mixture of equal parts by volume of He and H$_2$ at 1 atm pressure and at a total flow rate of 160 cc/min. The furnace temperature was ramped from room temperature to 650° C. at a heating rate of 15° C./min and held at temperature for 0.5 hours. The H$_2$/He flow was replaced with He and the heating continued to 1000° C. The flow rate was then replaced with a CO$_2$/CO/He mixture appropriate for the desired thermodynamic conversion. The conversion was allowed to proceed at 1000° C. for at least three hours. Finally the reactor was purged with He and cooled to room temperature. In this manner, the following four molybdenum eta phases were produced Fe$_6$Mo$_6$C, Co$_6$Mo$_6$C, Co$_6$Mo$_6$C (at an elevated temperature), and Ni$_6$MO$_6$C.

TABLE I

| | Molybdenum Eta Carbide Phases | | | | |
|---|---|---|---|---|---|
| Eta-Phase | Temp. (C.°) | CO$_2$ (cc/min) | CO (cc/min) | He (cc/min) | Carbon Activity | Pco+Pco (Torr) |
| Ni$_6$Mo$_6$C | 1000 | 64.8 | 200 | 200 | 0.011 | 433 |
| Co$_6$Mo$_6$C | 1000 | 64.8 | 200 | 200 | 0.011 | 433 |
| Fe$_6$Mo$_6$C | 1000 | 64.8 | 200 | 200 | 0.011 | 433 |
| Co$_6$Mo$_6$C | 1010 | 14.0 | 100 | 0 | 0.048 | 760 |

EXAMPLE 9

Thermodynamically Controlled Preparation of Tungsten Carbide Eta Phases

The reactive precursor for the synthesis of a pure Co$_6$W$_6$C was prepared by reductive decomposition of Co(en)$_3$WO$_4$. The transition metal coordination compound was placed in a quartz boat in a 1.5" I.D. quartz tubular furnace and heated in a flowing mixture of equal parts by volume of He and H$_2$ at 1 atm pressure and total flow rate of 160 cc/min. The furnace was ramped from room temperature to a temperature of 650° C. at a heating rate of 15° C./min, held there for three hours and cooled to room temperature in flowing gas. At room temperature, the reactive gas was replaced by helium at a flow rate of 40 cc/min. The resulting reactive precursor was subsequently passivated in He/O$_2$ gas mixtures by successive addition of O$_2$ of increasing concentration prior to removal from the furnace tube.

The reactive high surface area precursor produced by the low temperature reductive decomposition of Co(en)$_3$WO$_4$ described above was placed in a quartz boat in the center of a uniform hot zone of a quartz tubular furnace in flowing argon at 900 Torr pressure and 250 cc/min flow rate. The furnace temperature was raised rapidly to the conversion temperature (typically 700° to 1000° C.). The argon flow was quickly replaced by the CO$_2$/CO mixture with total pressure (P) and CO$_2$/CO ratio necessary to achieve the desired carbon and oxygen activities at the conversion temperatures. The sample was held isothermally in the flowing reactive gas at a flow rate of 500 cc/min for a time sufficient to allow complete equilibration of the carbon activity of the precursor with the flowing gas. The CO$_2$/CO gas mixture was then purged from the reaction tube by argon at a flow rate of 500 cc/min and the furnace was rapidly cooled to room temperature. Samples were removed at room temperature without passivation. It was determined that complete conversion to the pure Co$_6$W$_6$C eta carbide had occurred for the precursor processed at a carbon activity, ac, of 0.1.

EXAMPLE 10

Kinetically Controlled Preparation of Ni$_6$Mo$_6$Z$_a$ Eta Phase

A small quartz boat was filled with Ni(en)$_3$MoO$_4$. The boat was then placed into a 1.5" I.D. quartz tubular furnace which had been preheated to 700° C. and which contained a 1:1 H$_2$/He mixture flowing at 500 cc/min. The reactor was maintained at these conditions for 3 hours after which the resulting catalyst was cooled to room temperature in the flowing gas mixture. The catalyst was removed from the reactor without passivation. The structure of the catalyst was determined by x-ray powder diffraction and elemental analysis.

EXAMPLE 11

Kinetically Controlled Preparation of Fe$_3$Ni$_3$Mo$_6$Z$_a$, Where a=1 and Fe$_3$Ni$_3$Mo$_6$Z$_a$, Where a=2 Eta Phase A small quartz boat was filled with [Fe(en)$_3$]$_{0.5}$[Ni(en)$_3$]$_{0.5}$MoO$_4$. The boat was then placed into a 1.5" I.D. quartz tubular furnace which had been preheated to 700° C. and which contained He flowing at 500 cc/min. The temperature was allowed to stabilize and the flow increased to 525 cc/min with the addition of a H$_2$ gas stream. The reactor was maintained at these conditions for 3 hours after which the catalyst was cooled to room temperature in the flowing gas mixture. The catalyst was passivated at room temperature according to the following schedule.

2% $O_2$ in He for 1 hour
4% $O_2$ in He for 1 hour
6% $O_2$ in He for 15 minutes
10% $O_2$ in He for 15 minutes The samples were removed from the reactor. X-ray and chemical analysis showed that the catalyst sample contained two forms of eta phase catalyst, $Fe_3Ni_3Mo_6Z_a$, where a is greater than zero but less than or equal to 1 and $Fe_3Ni_3Mo_6Z_a$, where a is greater than zero but less than or equal to 2.

EXAMPLE 12

Molybdenum Nickel Eta Phase Catalyst for CO Hydrogenation: Effect of Pressure on Alcohol Synthesis Samples of eta phase catalysts were evaluated for CO hydrogenation reactions in a continuous flow unit with separate mass flow controllers for metering the feed rates of carbon monoxide and hydrogen to a stainless steel upflow reactor temperature controlled in a fluidized sand bath with 2.0 cc catalyst volume between porous frits. An on-line gas chromatograph was used for analyzing both reactants and products, and a back pressure regulator was used for controlling the reaction pressure between 1 and 60 atmospheres. A sample of molybdenum nickel eta phase catalyst weighing 0.53 g, prepared by the methods of Example 1 and Example 10, was loaded into the reactor and flushed with flowing hydrogen at room temperature. The catalyst was heated in stages, first to 120° C., then to 250° C. and finally to 400° C. The sample was reduced for at least 1 hour at 400° C. prior to lowering the temperature for reaction studies. A temperature of 250° C. was used as a typical temperature for evaluating new materials. The effect of pressure on catalyst performance of molybdenum nickel eta phase catalyst is shown in Table II. The feed rates were varied from 40 to 80 to 120 cc (STP) per minute as the pressure was increased from 1 to 5 to 10 to 15 atmospheres pressure. The $H_2$/CO ratio was maintained at 3.0. The product distribution changed substantially as the pressure was increased from 1 atmosphere. Initially the products were exclusively light hydrocarbons, water and $CO_2$. As the pressure was raised, substantial quantities of alcohols appeared in the products. Increasing the pressure increased the methanol selectivity from 29.8% to 46.1% to 52.2%.

TABLE II

| Molybdenum Nickel Eta Phase Catalyst | | | | |
|---|---|---|---|---|
| | Run Number | | | |
| | 2-1 | 2-2 | 2-3 | 2-4 |
| Temp.(°C.) | 249 | 250 | 252 | 249 |
| Pressure (atm) | 1.0 | 5.0 | 10.0 | 15.0 |
| $H_2$/CO inlet | 3.0 | 3.0 | 3.0 | 3.0 |
| Feed Rate (cc/min) | 40 | 40 | 80 | 120 |
| % CO Conversion | 1.2 | 2.8 | 2.3 | 1.9 |
| Product Selectivity (wt. %, $CO_2$ free) | | | | |
| $C_1$ hydrocarbons | 63.8 | 44.0 | 33.5 | 29.2 |
| $C_2$ hydrocarbons | 27.5 | 14.5 | 9.7 | 7.9 |
| $C_3$ hydrocarbons | 8.6 | 5.0 | 3.5 | 2.8 |
| $C_4$ hydrocarbons | — | 1.6 | 1.5 | 1.3 |
| $C_5$ hydrocarbons | — | 0.5 | 0.4 | 0.5 |
| $C_1$ alcohols | — | 29.8 | 46.1 | 52.2 |
| $C_2$ alcohols | — | 4.6 | 5.3 | 5.9 |
| $C_3$ alcohols | — | — | — | 0.3 |

EXAMPLE 13

Molybdenum Nickel Eta Phase Catalyst For CO Hydrogenation: Effect of Partial Pressure on Selectivity The sample of molybdenum nickel eta phase catalyst described in Example 12 was tested to determine the effect of $H_2$/CO ratio on performance. The catalyst sample was heated to 250° C. and the initial reactant inlet partial pressures were set at CO=1.0 atm and $H_2$=3.0 atm. Conversions were maintained at a low level so that the changes in reactant concentration would be low in moving from the reactor inlet to the outlet. The reactant concentrations were changed systematically, first by maintaining the CO partial pressure and increasing the hydrogenation pressure, then by holding the hydrogen partial pressure constant and increasing the CO partial pressure. The results of this set of runs are presented in Table III. The run 3-1 starting the sequence has $H_2$/CO=3.0 and a total pressure of 4.0 atm. Both hydrocarbons and alcohols are among the products. Increasing the $H_2$/CO ratio to 6.0 while maintaining the CO partial pressure increased the reaction rate and increased the selectivity to methanol relative to hydrocarbon products. Increasing the $H_2$/CO ratio to 9.0 increased the alcohol selectivity still further. When the $H_2$ partial pressure reached 9.0 atm, the CO partial pressure was systematically increased first to 2.0 atm, then 4.0 atm, and finally 6.0 atm. The $H_2$/CO ratio decreased from 9.0 to 1.5 over the full range. The high selectivity to light alcohols was maintained over this broad range of $H_2$/CO ratio.

TABLE III

| Molybdenum Nickel Eta Phase Catalyst | | | | | | |
|---|---|---|---|---|---|---|
| | Run Number | | | | | |
| | 3-1 | 3-2 | 303 | 3-4 | 3-5 | 3-6 |
| Temp. (°C.) | 253 | 253 | 252 | 256 | 252 | 252 |
| Total Pressure (atm) | 4.0 | 7.0 | 10.0 | 11.0 | 13.0 | 15.0 |
| $H_2$ Pressure (atm) | 3.0 | 6.0 | 9.0 | 9.0 | 9.0 | 9.0 |
| CO Pressure (atm) | 1.0 | 1.0 | 1.0 | 2.0 | 4.0 | 6.0 |
| $H_2$/CO inlet | 3.0 | 6.0 | 9.0 | 4.5 | 2.2 | 1.5 |
| Feed Rate (cc/min) | 40 | 70 | 100 | 110 | 130 | 150 |
| % CO Conversion | 1.8 | 2.9 | 4.4 | 2.2 | 1.1 | 0.7 |
| Product Selectivity (wt. %, $CO_2$ free) | | | | | | |
| $C_1$ hydrocarbons | 46.1 | 40.0 | 38.8 | 33.4 | 29.7 | 27.2 |
| $C_2$ hydrocarbons | 15.8 | 10.6 | 8.8 | 8.5 | 8.5 | 8.7 |
| $C_3$ hydrocarbons | 5.3 | 3.1 | 2.5 | 2.7 | 3.0 | 3.2 |
| $C_4$ hydrocarbons | 1.2 | 0.5 | 0.5 | 1.4 | 1.3 | 1.2 |
| $C_5$ hydrocarbons | 0.4 | 0.3 | 0.3 | 0.2 | 0.4 | 0.5 |

TABLE III-continued

| | Molybdenum Nickel Eta Phase Catalyst | | | | | |
|---|---|---|---|---|---|---|
| | Run Number | | | | | |
| | 3-1 | 3-2 | 303 | 3-4 | 3-5 | 3-6 |
| $C_1$ alcohols | 31.2 | 41.4 | 46.3 | 49.2 | 51.2 | 51.4 |
| $C_2$ alcohols | — | 4.0 | 2.9 | 4.7 | 5.9 | 7.9 |
| $C_3$ alcohols | — | — | — | — | — | — |

EXAMPLE 14

Molybdenum Nickel Eta Phase Catalyst For CO Hydrogenation: Effect of Temperature on Selectivity A 0.51 g sample of molybdenum nickel eta phase catalyst was evaluated at constant pressure and $H_2/CO$ ratio while the temperature was varied. Table IV shows changes in the rate and product distribution when the reaction temperature was increased from 199 to 302° C. The $H_2/CO$ ratio was maintained at 3.0 and the total pressure was 10 atmospheres. Run 4-1 shows high selectivity to methanol at 199° C. This selectivity stayed at 49% when the temperature was increased to 250° C., but dropped to 38% at 275° C. and to 12% at 302° C. Decreased selectivity to methanol at the higher temperatures was predicted by thermodynamic considerations. Higher reaction temperatures require higher pressures to prevent methanol from decomposing to the reactants $CO+2H_2$. Increased reaction temperature has a substantial effect on the rate of CO conversion to hydrocarbons.

TABLE IV

| | Molybdenum Nickel Eta Phase Catalyst | | | |
|---|---|---|---|---|
| | Run Number | | | |
| | 4-1 | 4-2 | 4-3 | 4-4 |
| Temp.(°C.) | 199 | 250 | 275 | 302 |
| Pressure (atm) | 10.0 | 10.0 | 10.0 | 10.0 |
| $H_2/CO$ inlet | 3.0 | 3.0 | 3.0 | 3.0 |
| Feed Rate (cc/min) | 40 | 80 | 120 | 120 |
| % CO Conversion | 0.8 | 2.5 | 4.2 | 12.0 |
| Product Selectivity (wt. %, $CO_2$ free) | | | | |
| $C_1$ hydrocarbons | 24.2 | 32.6 | 46.4 | 74.2 |
| $C_2$ hydrocarbons | 9.2 | 7.5 | 7.9 | 8.8 |
| $C_3$ hydrocarbons | 5.4 | 3.1 | 2.5 | 2.7 |
| $C_4$ hydrocarbons | 2.7 | 1.0 | 0.9 | 0.8 |
| $C_5$ hydrocarbons | 1.3 | 1.1 | 0.5 | 0.3 |
| $C_{5+}$ hydrocarbons | 2.1 | 0.6 | 0.5 | 0.4 |
| $C_1$ alcohols | 49.0 | 49.1 | 38.2 | 11.7 |
| $C_2$ alcohols | 6.2 | 5.0 | 2.9 | 1.1 |
| $C_3$ alcohols | — | — | — | — |

EXAMPLE 15

Comparison of Molybdenum Nickel Eta Phase With Molybdenum Oxycarbonitride for CO Hydrogenation A comparison of the catalytic properties of molybdenum nickel eta phase was made with molybdenum oxycarbonitride for CO hydrogenation reactions. Molybdenum oxycarbonitride is a high surface area, high activity catalyst for CO hydrogenation as described in U.S. Pat. No. 4,418,154. It produces hydrocarbon product distributions typical of traditional molybdenum carbide and molybdenum nitride materials, but has high activity due to its high surface area. A comparison of 1.08 g of molybdenum oxycarbonitride with 0.53 g of molybdenum nickel eta phase catalyst using the continuous flow unit described in Example 12 is shown in Table V. At 250° C., 10 atmospheres pressure, and a $H_2/CO$ ratio of 1.0, the molybdenum nickel eta phase catalyst produced a product distribution containing 46.3% hydrocarbons and 53.7% alcohols. By contrast, the molybdenum oxycarbonitride catalyst produced 94.5% hydrocarbons and only 5.5% alcohols. The high selectivity to alcohols distinguishes the molybdenum eta phase catalyst from catalyst containing molybdenum alone in a carbide, nitride, oxycarbide, carbonitride, or oxycarbonitride form.

TABLE V

| | Comparison of Molybdenum Nickel Eta Phase With Molybdenum Oxycarbonitride For CO Hydrogenation | |
|---|---|---|
| | Run Number | |
| | 5-1 | 5-2 |
| | Catalyst | |
| | MoNi eta phase | $MoOxC_yN_z$ |
| Temp. (°C.) | 250 | 249 |
| Pressure (atm) | 10.0 | 10.0 |
| $H_2/CO$ inlet | 1.0 | 1.0 |
| Feed Rate (cc/min) | 100 | 120 |
| % CO Conversion | 0.66 | 1.60 |
| Product Selectivity (wt. %, $CO_2$ free) | | |
| $C_1$ hydrocarbons | 28.0 | 50.2 |
| $C_2$ hydrocarbons | 10.8 | 18.9 |
| $C_3$ hydrocarbons | 4.4 | 8.5 |
| $C_4$ hydrocarbons | 1.5 | 3.2 |
| $C_5$ hydrocarbons | 0.8 | 1.6 |
| $C_{5+}$ hydrocarbons | 0.9 | 12.2 |
| $C_1$ alcohols | 37.5 | 5.1 |
| $C_2$ alcohols | 14.4 | 0.4 |
| $C_3$ alcohols | 1.3 | — |
| $C_4$ alcohols | 0.5 | — |

EXAMPLE 16

Molybdenum Cobalt Eta Phase Catalyst For CO Hydrogenation: Effect of Temperature on Selectivity A 0.51 g sample of molybdenum cobalt eta phase catalyst was evaluated at constant pressure and $H_2/CO$ ratio while the temperature was varied. Table VI shows how rate and product distribution changed when the reaction temperature was increased from 203° to 299° C. The $H_2/CO$ inlet ratio was maintained at 3.0 and the total pressure was 10 atmospheres. Run 6-1 shows product selectivities for both hydrocarbons and alcohols. The major individual product at 203° C. is methanol. A comparison of molybdenum cobalt with molybdenum nickel at similar conditions shows that changing from nickel to cobalt increased the hydrocarbon yield relative to alcohols and also caused the hydrocarbon distribution to shift toward higher molecular weights. Increasing reaction temperature increases reaction rates and selectivities toward hydrocarbons.

TABLE VI

| | Molybdenum Cobalt Eta Phase Catalyst | | | |
|---|---|---|---|---|
| | Run Number | | | |
| | 6-1 | 6-2 | 6-3 | 6-4 |
| Temp.(°C.) | 203 | 250 | 275 | 299 |
| Pressure (atm) | 10.0 | 10.0 | 10.0 | 10.0 |

TABLE VI-continued

| Molybdenum Cobalt Eta Phase Catalyst | | | | |
|---|---|---|---|---|
| | Run Number | | | |
| | 6-1 | 6-2 | 6-3 | 6-4 |
| $H_2/CO$ inlet | 3.0 | 3.0 | 3.0 | 3.0 |
| Feed Rate (cc/min) | 120 | 120 | 120 | 120 |
| % CO Conversion | 0.8 | 9.6 | 20.4 | 54.2 |
| Product Selectivity (wt. %, $CO_2$ free) | | | | |
| $C_1$ hydrocarbons | 17.1 | 32.0 | 44.1 | 57.9 |
| $C_2$ hydrocarbons | 13.4 | 19.9 | 23.4 | 24.8 |
| $C_3$ hydrocarbons | 11.1 | 12.4 | 11.9 | 9.8 |
| $C_4$ hydrocarbons | 6.2 | 5.8 | 4.7 | 3.1 |
| $C_5$ hydrocarbons | 4.1 | 3.2 | 2.3 | 1.4 |
| $C_{5+}$ hydrocarbons | 10.3 | 7.7 | 5.3 | 2.2 |
| $C_1$ alcohols | 29.3 | 14.5 | 7.5 | 0.7 |
| $C_2$ alcohols | 8.5 | 4.2 | 0.9 | 0.1 |
| $C_3$ alcohols | — | 0.3 | — | — |

EXAMPLE 17

Molybdenum Cobalt Eta Phase Catalyst For CO Hydrogenation: Effect of Reactant Partial Pressure on Selectivity A 0.51 g sample of molybdenum cobalt eta phase catalyst was tested to determine the effect of $H_2/CO$ ratio on performance. The catalyst sample was heated to 250° C. and the initial reactant inlet partial pressures were set at CO = 1.0 atm and $H_2$ = 3.0 atm. The reactant concentrations were changed systematically, first by maintaining the CO partial pressure and increasing the hydrogen pressure, then by holding the hydrogen partial pressure constant and increasing the CO partial pressure. The results of this set of experiments are presented in Table VII. The run 7-1 starting the sequence has $H_2/CO$ 3.0 and a total pressure of 4 atm. Both hydrocarbons and alcohols are among the products. Increasing the $H_2/CO$ ratio to 6.0 while maintaining the CO partial pressure increased reaction rates and increased selectivity towards alcohols. The hydrocarbon product distribution became slightly lighter with increasing hydrogen partial pressure. Increasing the $H_2/CO$ ratio to 9.0 continued the trend toward more alcohols and lighter hydrocarbon products. When the $H_2$ inlet partial pressure reached 9.0 atm, the CO inlet partial pressure was systematically increased, first to 2.0 atm and then to 4.0 atm. Increased CO pressure reduced the catalyst selectivity toward methane and increased selectivity toward methanol and other light alcohols.

TABLE VII

| Molybdenum Cobalt Eta Phase Catalyst | | | | | |
|---|---|---|---|---|---|
| | Run Number | | | | |
| | 7-1 | 7-2 | 7-3 | 7-4 | 7-5 |
| Temp.(°C.) | 249 | 247 | 254 | 247 | 248 |
| Pressure (atm) | 4.0 | 7.0 | 10.0 | 11.0 | 13.0 |
| $H_2$ Pressure | 3.0 | 6.0 | 9.0 | 9.0 | 9.0 |
| CO Pressure | 1.0 | 1.0 | 1.0 | 2.0 | 4.0 |
| $H_2/CO$ inlet | 3.0 | 6.0 | 9.0 | 9.0 | 9.0 |
| Feed Rate (cc/min) | 40 | 70 | 100 | 110 | 130 |
| % CO Conversion | 11.2 | 15.3 | 20.5 | 8.5 | 3.9 |
| Product Selectivity (wt. %, $CO_2$ free) | | | | | |
| $C_1$ hydrocarbons | 33.5 | 40.5 | 45.3 | 35.2 | 28.9 |
| $C_2$ hydrocarbons | 25.7 | 22.3 | 20.4 | 19.4 | 18.2 |
| $C_3$ hydrocarbons | 16.7 | 11.9 | 10.0 | 11.0 | 11.4 |
| $C_4$ hydrocarbons | 7.4 | 5.1 | 4.1 | 4.5 | 5.0 |
| $C_5$ hydrocarbons | 4.2 | 2.5 | 1.8 | 2.5 | 2.9 |
| $C_{5+}$ hydrocarbons | 10.0 | 7.2 | 4.7 | 5.8 | 7.2 |
| $C_1$ alcohols | 2.6 | 9.5 | 12.6 | 17.8 | 19.7 |
| $C_2$ alcohols | — | 1.1 | 1.2 | 3.7 | 6.2 |

TABLE VII-continued

| Molybdenum Cobalt Eta Phase Catalyst | | | | | |
|---|---|---|---|---|---|
| | Run Number | | | | |
| | 7-1 | 7-2 | 7-3 | 7-4 | 7-5 |
| $C_3$ alcohols | — | — | — | 0.2 | 0.6 |

EXAMPLE 18

Molybdenum Iron Eta Phase Catalyst For CO Hydrogenation

A 0.50 g sample of molybdenum iron eta phase catalyst was tested in the continuous flow reactor described in Example 12 to determine its activity and selectivity for $H_2/CO$ reactions. Tests were carried out at 10.0 atm pressure and a constant inlet $H_2/CO$ ratio of 3.0 while the temperature was varied. Table VIII shows how the conversion and product distributions changed as the temperature was increased from 200 to 302° C. Run 8-1 shows that at 200° C. the iron molybdenum eta phase catalyst has low methane selectivity, a broad distribution of hydrocarbon products, and high selectivity to both methanol and ethanol. Catalyst samples containing iron had broader product distributions than their analogs containing cobalt (run 6-1) or nickel (run 4-1). Increasing reaction temperature at 10 atm pressure increased reaction rate and shifted the product distribution toward lower molecular weights.

TABLE VIII

| Molybdenum Iron Eta Phase Catalyst | | | |
|---|---|---|---|
| | Run Number | | |
| | 8-1 | 8-2 | 8-3 |
| Temp.(°C.) | 200 | 249 | 302 |
| Pressure (atm) | 10.0 | 10.0 | 10.0 |
| $H_2/CO$ inlet | 3.0 | 3.0 | 3.0 |
| Feed Rate (cc/min) | 40 | 80 | 120 |
| % CO Conversion | 3.2 | 9.7 | 38.4 |
| Product Selectivity (wt. %, $CO_2$ free) | | | |
| $C_1$ hydrocarbons | 15.0 | 25.6 | 44.5 |
| $C_2$ hydrocarbons | 11.4 | 17.9 | 26.2 |
| $C_3$ hydrocarbons | 11.5 | 14.4 | 14.2 |
| $C_4$ hydrocarbons | 7.2 | 7.3 | 5.6 |
| $C_5$ hydrocarbons | 5.5 | 4.4 | 2.9 |
| $C_{5+}$ hydrocarbons | 19.4 | 12.4 | 6.6 |
| $C_1$ alcohols | 15.2 | 12.7 | 0.8 |
| $C_2$ alcohols | 12.4 | 4.5 | 0.2 |
| $C_3$ alcohols | 2.5 | 0.9 | — |

EXAMPLE 19

Preparation of Potassium Promoted Molybdenum Iron Eta Phase Catalyst

A 0.487 M solution of potassium carbonate was prepared by dissolving 1.01 g of potassium carbonate in 15.0 g of distilled water. 0.87 cc of the resulting solution was added dropwise to 0.99 g of molybdenum iron eta phase catalyst. The sample was stirred to provide an even distribution of liquid over the solid sample and then permitted to air dry. The concentration of potassium on the sample is calculated to be 3.2%.

EXAMPLE 20

Potassium Promoted Molybdenum Iron Eta Phase Catalyst For CO Hydrogenation: A Comparison With Unpromoted Molybdenum Iron Eta Phase Catalyst A 0.51 g sample of potassium promoted molybdenum iron eta phase catalyst was tested at conditions similar to those used in Example 18 to determine the effect of the potassium addition on the catalyst performance. The comparison was made at 10.0 atm total pressure, a $H_2/CO$ ratio of 3.0 and at both 250 and 300° C. The results were presented in Table IX. At approximately 250° C., the potassium promoted catalyst showed a substantially heavier product than the unpromoted sample. Methane selectivity was 12.8% as compared to 25.6%. The heavier hydrocarbon liquids were analyzed at 16.9% as compared to 12.4%, and the alcohol selectivity showed a substantial increase with potassium addition. At 300° C., similar results were observed with methane from the potassium promoted sample being about half that produced by the unpromoted sample. Again, heavier hydrocarbon liquids were observed, as well as substantially more alcohol products.

TABLE IX

Potassium Promoter Affects on Molybdenum Iron Eta Phases

| | Run Number | | | |
|---|---|---|---|---|
| | 9-1 | 8-2 | 9-2 | 8-3 |
| % Potassium | 3.2 | 0.0 | 3.2 | 0.0 |
| Temp.(°C.) | 253 | 249 | 304 | 302 |
| Pressure (atm) | 10.0 | 10.0 | 10.0 | 10.0 |
| $H_2/CO$ inlet | 3.0 | 3.0 | 3.0 | 3.0 |
| Feed Rate (cc/min) | 80 | 80 | 80 | 80 |
| % CO Conversion | 1.0 | 9.7 | 5.0 | 38.4 |
| Product Selectivity (wt. %, $CO_2$ free) | | | | |
| $C_1$ hydrocarbons | 12.8 | 25.6 | 22.4 | 44.5 |
| $C_2$ hydrocarbons | 12.9 | 17.9 | 19.9 | 26.2 |
| $C_3$ hydrocarbons | 9.8 | 14.4 | 12.6 | 14.2 |
| $C_4$ hydrocarbons | 6.2 | 7.3 | 6.7 | 5.6 |
| $C_5$ hydrocarbons | 4.8 | 4.4 | 4.9 | 2.9 |
| $C_{5+}$ hydrocarbons | 16.9 | 12.4 | 11.8 | 6.6 |
| $C_1$ alcohols | 19.0 | 12.7 | 10.6 | 0.8 |
| $C_2$ alcohols | 16.3 | 4.5 | 9.9 | 0.2 |
| $C_3$ alcohols | 1.4 | 0.9 | 1.3 | — |

EXAMPLE 21

Molybdenum Nickel-Iron Eta Phase Catalyst For CO Hydrogenation

A 0.50 g sample of molybdenum nickel-iron eta phase catalyst as prepared in Example 11 was evaluated at constant pressure and $H_2/CO$ ratio while the temperature was varied. Table X shows how rate and product distribution changed when the reaction temperature was increased from 199° to 300° C. The $H_2/CO$ inlet ratio was 3.0 and the total pressure was 10.0 atm. The product contains both hydrocarbons and alcohols. At 199° C., the major product is methanol. Raising the temperature reduces the selectivity to alcohols with hydrocarbons being the predominant product at 300° C.

TABLE X

Molybdenum Nickel-Iron Eta Phase Catalyst

| | Run Number | | |
|---|---|---|---|
| | 10-1 | 10-2 | 10-3 |
| Temp.(°C.) | 199 | 251 | 300 |
| Pressure (atm) | 10.0 | 10.0 | 10.0 |
| $H_2/CO$ inlet | 3.0 | 3.0 | 3.0 |
| Feed Rate (cc/min) | 40 | 80 | 120 |
| % CO Conversion | 2.6 | 6.9 | 25.9 |
| Product Selectivity (wt. %, $CO_2$ free) | | | |
| $C_1$ hydrocarbons | 18.8 | 30.8 | 52.3 |
| $C_2$ hydrocarbons | 12.0 | 16.1 | 22.0 |
| $C_3$ hydrocarbons | 9.2 | 9.9 | 10.4 |
| $C_4$ hydrocarbons | 5.4 | 4.8 | 4.3 |
| $C_5$ hydrocarbons | 2.9 | 2.6 | 2.1 |
| $C_{5+}$ hydrocarbons | 7.8 | 6.1 | 4.5 |
| $C_1$ alcohols | 29.5 | 22.3 | 3.9 |
| $C_2$ alcohols | 12.5 | 6.5 | 0.5 |
| $C_3$ alcohols | 2.0 | 1.0 | — |

EXAMPLE 22

Comparison of Molybdenum Eta Phase Catalysts For CO Hydrogenation Reactions: Effect of Group VIII Metals on Selectivity A comparison of the molybdenum eta phase catalysts described in Examples 14, 16, 18 and 21 is made in Table XI. The molybdenum nickel-iron eta phase catalyst is compared with its molybdenum nickel, molybdenum cobalt and molybdenum iron analogs. The comparison is made for reactions at approximately 250° C., 10.0 atm pressure and $H_2/CO=3.0$. All of the catalyst make similar products, but variations do occur in a systemic way. Molybdenum nickel is most selective to methanol. Methanol selectivity decreases as the Group VIII metal changes from nickel to cobalt to iron. While methanol selectivity is decreasing, the hydrocarbon products are becoming more significant, and they are shifting from primarily light products to heavier products. Comparing the mixed Group VIII metal eta phase catalyst to the others, the nickel-iron combination produces a product state similar to that produced by cobalt. The mixed Group VIII metal eta phase catalyst is clearly not just the average of nickel properties and iron properties, for were that the case, yield of methanol would be higher. This similarity between molybdenum nickel-iron and molybdenum cobalt can also be observed at 200° and 300° C. by comparing the data provided in Table X with Table VI.

TABLE XI

Comparison of Molybdenum Eta Phase Catalysts

| | Run Number | | | |
|---|---|---|---|---|
| | 10-2 | 4-2 | 6-2 | 8-2 |
| | Group VIII Metals | | | |
| | NiFe | Ni | Co | Fe |
| Temp.(°C.) | 251 | 250 | 250 | 249 |
| Pressure (atm) | 10.0 | 10.0 | 10.0 | 10.0 |
| $H_2/CO$ inlet | 3.0 | 3.0 | 3.0 | 3.0 |
| Feed Rate (cc/min) | 80 | 80 | 120 | 80 |
| % CO Conversion | 6.9 | 2.5 | 9.6 | 9.7 |
| Product Selectivity (wt. %, $CO_2$ free) | | | | |
| $C_1$ hydrocarbons | 30.8 | 32.6 | 32.0 | 25.6 |
| $C_2$ hydrocarbons | 16.1 | 7.5 | 19.9 | 17.9 |
| $C_3$ hydrocarbons | 9.9 | 3.1 | 12.4 | 14.4 |
| $C_4$ hydrocarbons | 4.8 | 1.0 | 5.8 | 7.3 |
| $C_5$ hydrocarbons | 2.6 | 1.1 | 3.2 | 4.4 |
| $C_{5+}$ hydrocarbons | 6.1 | 0.6 | 7.7 | 12.4 |
| $C_1$ alcohols | 22.3 | 49.1 | 14.5 | 12.7 |
| $C_2$ alcohols | 6.5 | 5.0 | 4.2 | 4.5 |
| $C_3$ alcohols | 1.0 | — | 0.3 | 0.9 |

EXAMPLE 23

Tungsten Nickel Eta Phase Catalysts For CO Hydrogenation

A 1.02 g sample of tungsten nickel eta phase catalyst was evaluated at constant pressure and $H_2/CO$ ratio while the temperature was varied. Table XII shows how rate and product distribution changed when the temperature was increased from 172° to 252° C. The $H_2/CO$ ratio was maintained at 3.0 and the total pressure was maintained at 10 atm. Run 12-1 shows high selectivity to methanol at 172° C. This initial selectivity of 28% methanol remained nearly constant as the temperature was increased to 223° C., then decreased slightly to 20% on raising the reaction temperature to 252° C. The hydrocarbon distribution is comprised primarily of methane and other light hydrocarbon products.

TABLE XII

| | Tungsten Nickel Eta Phase Catalyst | | | |
|---|---|---|---|---|
| | Run Number | | | |
| | 12-1 | 12-2 | 12-3 | 12-4 |
| Temp.(°C.) | 172 | 199 | 223 | 252 |
| Pressure (atm) | 10.0 | 10.0 | 10.0 | 10.0 |
| $H_2/CO$ inlet | 3.0 | 3.0 | 3.0 | 3.0 |
| Feed Rate (cc/min) | 40 | 40 | 40 | 40 |
| % CO Conversion | 0.73 | 1.7 | 2.1 | 6.0 |
| Product Selectivity (wt. %, $CO_2$ free) | | | | |
| $C_1$ hydrocarbons | 45.0 | 46.8 | 53.3 | 65.2 |
| $C_2$ hydrocarbons | 12.8 | 11.1 | 10.2 | 9.0 |
| $C_3$ hydrocarbons | 5.1 | 4.1 | 3.6 | 2.7 |
| $C_4$ hydrocarbons | 1.6 | 1.2 | 1.0 | 0.6 |
| $C_5$ hydrocarbons | 0.7 | 0.4 | 0.5 | 0.3 |
| $C_{5+}$ hydrocarbons | 2.1 | 0.7 | 0.9 | 0.3 |
| $C_1$ alcohols | 28.1 | 31.1 | 27.8 | 20.5 |
| $C_2$ alcohols | 4.6 | 4.6 | 2.6 | 1.4 |
| $C_3$ alcohols | — | — | — | — |

EXAMPLE 24

Tungsten Cobalt Eta Phase Catalysts For CO Hydrogenation

A 1.02 g sample of tungsten cobalt eta phase catalyst was evaluated at constant pressure and $H_2/CO$ ratio while the temperature was varied. Table XIII shows rate and product distribution changes when the temperature was increased from 201° to 304° C. The $H_2/CO$ ratio was maintained at 3.0 and the total pressure was maintained at 10 atm. Run 13-1 shows high selectivity to light hydrocarbons and alcohols at 201° C. Increasing the temperature increases conversion and shifts both the hydrocarbons and alcohols toward lighter products.

TABLE XIII

| | Tungsten Cobalt Eta Phase Catalyst | | | | |
|---|---|---|---|---|---|
| | Run Number | | | | |
| | 13-1 | 13-2 | 13-3 | 13-4 | 13-5 |
| Temp.(°C.) | 201 | 227 | 252 | 278 | 304 |
| Pressure (atm) | 10.0 | 10.0 | 10.0 | 10.0 | 10.0 |
| $H_2/CO$ inlet | 3.0 | 3.0 | 3.0 | 3.0 | 3.0 |
| Feed Rate (cc/min) | 40 | 40 | 40 | 80 | 120 |
| % CO Conversion | 1.5 | 4.2 | 10.3 | 13.1 | 20.9 |
| Product Selectivity (wt. %, $CO_2$ free) | | | | | |
| $C_1$ hydrocarbons | 27.1 | 29.9 | 36.6 | 44.0 | 4.5 |
| $C_2$ hydrocarbons | 18.1 | 20.1 | 23.0 | 25.1 | 26.4 |
| $C_3$ hydrocarbons | 13.7 | 13.3 | 13.6 | 12.7 | 10.5 |
| $C_4$ hydrocarbons | 6.9 | 6.1 | 5.7 | 4.7 | 3.3 |
| $C_5$ hydrocarbons | 3.6 | 3.9 | 3.2 | 2.4 | 1.5 |
| $C_{5+}$ hydrocarbons | 9.9 | 9.2 | 7.4 | 5.3 | 3.3 |
| $C_1$ alcohols | 12.9 | 11.2 | 8.4 | 4.6 | 0.6 |
| $C_2$ alcohols | 7.8 | 6.3 | 2.0 | 1.2 | — |
| $C_3$ alcohols | — | — | — | — | — |

EXAMPLE 25

1-Hexene Hydrogenation With Tungsten Cobalt Eta Phase Catalyst

Samples of eta phase catalyst were evaluated for olefin hydrogenation in a continuous flow unit with mass flow controllers for metering flows of hydrogen and helium, a gas saturator in a constant temperature bath for adding controlled amounts of hydrocarbons to the hydrogen or helium stream, a stainless steel upflow reactor temperature controlled in a sand bath with 2.0 cc catalyst volume between porous frits, an on line gas chromatograph for analyzing both reactants and products, and a back pressure regulator for controlling the reaction pressure between 1 and 60 atmospheres. A sample of tungsten cobalt eta phase catalyst weighing 1.02 g was loaded into the reactor and reduced in flowing hydrogen at 90 cc/min (STP) at 400° C. for 1.5 hours. The reactor temperature was lowered to room temperature to evaluate this material as a catalyst for olefin hydrogenation. The unit was pressurized to 9.9 atmospheres with hydrogen, the saturator filled with 1-hexene and thermostated to 0° C., and the hydrogen flow rate controlled at 50 cc/min (STP). The saturator temperature set the 1-hexene concentration at 0.7 volume percent, a weight hourly space velocity of approximately 0.08 grams of feed per gram of catalyst per hour. Run 14-1 shows that 11 0% of the 1-hexene fed was hydrogenated to n-hexane at 24° C. The olefins that were not hydrogenated were isomerized so that the product contained not only 1-hexene and n-hexane but also 2-hexenes and 3-hexenes as well. The reactor temperature was raised to 97° C. and all of the feed was hydrogenated to n-hexane at this temperature. No methane or light hydrocarbon products indicative of carbon-carbon bond hydrogenolysis were observed. The results and conditions for these experiments are listed in Table XIV.

TABLE XIV

| | Tungsten Cobalt Eta Phase Catalyst | | |
|---|---|---|---|
| | Run Number | | |
| | feed | 14-1 | 14-2 |
| Temp.(°C.) | — | 24 | 97 |
| Pressure (atm) | — | 9.9 | 9.9 |
| $H_2$ Feed Rate (cc/min) | — | 50 | 50 |
| $H_2$/HC inlet | — | 140 | 140 |
| WHSV (g/g/hr)* | — | 0.08 | 0.08 |
| Analysis (wt. %) | | | |
| n-hexane | 0.0 | 11.0 | 100.0 |
| hexenes | 100.0 | 89.0 | 0.00 |
| $CH_4$ | 0.00 | 0.00 | 0.00 |
| Other $C_2$-$C_6$ | 0.00 | 0.00 | 0.00 |

*weight hourly space velocity

EXAMPLE 26

Benzene Hydrogenation With Tungsten Nickel Eta Phase Catalyst

Samples of eta phase catalyst were evaluated for aromatics hydrogenation and carbon-carbon bond hydrogenolysis in a continuous flow unit with mass flow controllers for metering flows of hydrogen and helium, a liquid chromatrography pump for maintaining low feed rates of liquid reactants, a stainless steel upflow reactor temperature controlled in a sand bath with 2.0 cc catalyst volume between porous frits, an on line gas chromatograph for analyzing both reactants and products, and a back pressure regulator for controlling the reaction between 1 and 60 atmospheres. A sample of tungsten nickel eta phase catayslt weighing 1.00 g was loaded into the reactor and reduced in flowing hydrogen at 80 cc/min (STP) at 400° C. for 2.5 hours. The reactor temperature was lowered to 250° C. to evaluate this material as a catalyst for benzene hydrogenation. The unit was pressurized to 21.3 atmospheres with hydrogen and a benzene feed was introduced at 0.50 g/hr, at weight hourly space velocity of 0.5 grams of feed per gram of catalyst per hour. Run 15-1 shows that all of the benzene was hydrogenated to cyclohexane at these conditions. None of the cyclohexane was cracked by carbon-carbon bond hydrogenolysis to lighter products at 252° C. The reactor temperature was lowered to 201° C. to reduce reaction rate. Again 100% of the benzene was hydrogenated to cyclohexane. Finally the reactor was cooled to 152° C. where the conversion of benzene to cyclohexane was again 100%. The results and conditions for these experiments are listed below in Table XV.

TABLE XV

Tungsten Nickel Eta Phase Catalyst

| | feed | Run Number | | |
| --- | --- | --- | --- | --- |
| | | 15-1 | 15-2 | 15-3 |
| Temp.(°C.) | — | 255 | 201 | 152 |
| Pressure (atm) | — | 21.3 | 21.3 | 21.3 |
| H$_2$ Feed Rate (cc/min) | — | 80 | 80 | 80 |
| HC Feed Rate (g/hr) | — | 0.50 | 0.50 | 0.50 |
| H$_2$/HC inlet | — | 33 | 33 | 33 |
| WHSV (g/g/hr)* | — | 0.5 | 0.5 | 0.5 |
| Analysis (wt. %) | | | | |
| cyclohexane | 0.07 | 100.0 | 100.0 | 100.0 |
| benzene | 97.93 | 0.00 | 0.00 | 0.00 |
| CH$_4$ | 0.00 | 0.00 | 0.00 | 0.00 |
| Other C$_2$-C$_6$ | 0.00 | 0.00 | 0.00 | 0.00 |

*weight hourly space velocity

EXAMPLE 27

Aromatics Hydrogenation With Tungsten Nickel Eta Phase Catalyst

The tungsten nickel eta phase catalyst used for Example 26 was tested again for aromatics hydrogenation using a mixture comprised of 14.6% naphthylene in benzene. The reactor temperature was raised from room temperature to 250° C. and the unit pressurized with hydrogen to 21.3 atm. The aromatic feed mixture was introduced at 1.33 g/hr, a weight hourly space velocity of 1.33 grams of feed per gram of catalyst per hour. Introducing the feed at this rate raised the reaction temperature above that of the sand bath. Run 16-1 shows that at 267° C., 99.98% of the benzene was hydrogenated to cyclohexane and 99.66% of the naphthylene was hydrogenated to either tetralin (1.7%) or one of the decalin isomers (98%). Only traces of other hydrocarbon products due to either isomerization or carbon-carbon bond hydrogenolysis were observed. Raising the reaction temperature from 267° to 313° C. caused the extent of aromatic hydrogenation to decrease since increasing temperature shifts the thermodynamic equilibrium away from the totally hydrogenated product and toward the aromatic forms. Raising the temperature caused only a small increase in carbon-carbon bond breaking or skeletal rearrangements. The methane product was only 0.03% while the total hydrocarbon converted to other structural forms was 1.3%. A final increase in reaction temperature to 361° C. reduced aromatics saturation still further due to changing equilibrium position and increased the extent of rearranged or cracking products to 6.3%.

TABLE XVI

Tungsten Nickel Eta Phase Catalyst

| | feed | Run Number | | |
| --- | --- | --- | --- | --- |
| | | 16-1 | 16-2 | 16-3 |
| Temp.(°C.) | — | 267 | 313 | 361 |
| Pressure (atm) | — | 21.3 | 21.3 | 21.3 |
| H$_2$ Feed Rate (cc/min) | — | 80 | 80 | 80 |
| HC Feed Rate (g/hr) | — | 1.33 | 1.33 | 1.33 |
| H$_2$/HC inlet | — | 13 | 13 | 13 |
| WHSV (g/g/hr)* | — | 1.33 | 1.33 | 1.33 |
| Analysis (wt. %) | | | | |
| cyclohexane | 0.06 | 85.20 | 67.25 | 32.76 |
| benzene | 85.21 | 0.02 | 16.71 | 51.13 |
| trans-decalin | 0.01 | 9.26 | 9.86 | 4.51 |
| cis-decalin | 0.02 | 5.15 | 3.74 | 1.85 |
| tetralin | 0.08 | 0.25 | 1.06 | 2.58 |
| naphthalene | 14.61 | 0.05 | 0.11 | 0.92 |
| CH$_4$ | 0.00 | 0.00 | 0.03 | 0.56 |
| Other C$_2$-C$_6$ | 0.00 | 0.05 | 0.46 | 2.19 |
| Other C$_7$-C$_{10}$ | 0.00 | 0.02 | 0.78 | 3.49 |

*weight hourly space velocity

EXAMPLE 28

Methylcyclohexane Conversion With Tungsten Cobalt Eta Phase Catalyst

A tungsten cobalt eta phase catalyst was tested for converting cycloparaffins to aromatics and isoparaffins. Using the catalyst and test unit described in Example 25, methylcyclohexane was added to the saturator thermostated at 0° C., the pressure was raised to 350° C. A hydrogen flow of 50 cc/min (STP) carrying 0.16 volume percent methylcyclohexane made the weight hourly space velocity of hydrocarbons approximately 0.02 grams of feed per gram of catalyst per hour. Run 17-1 shows that at 351° C., about 56% of the methylcyclohexane had reacted, yielding 8.1% toluene, 42.8% heptane isomers, and 5.2% methane. Toluene was the dehydrogenation product, the other C$_7$'s were paraffins produced by isomerization of the methylcyclohexane, and the methane and other C$_2$-C$_6$'s were products of carbon-carbon bond hydrogenolysis and various conversion reactions. Raising the temperature to 401° C. increased the toluene selectivity to 53% with lower selectivity to other C$_7$ paraffin isomers. Both benzene and xylene products were evident as well as hydrogenolysis products of methane and C$_2$-C$_6$ paraffins. The tungsten cobalt eta phase catalyst showed only 10.2% methane and C$_2$-C$_6$ paraffins under conditions where most of the products were either aromatics or branched C$_7$ paraffin isomers.

TABLE XVII

Tungsten Cobalt Eta Phase Catalyst

| | feed | Run Number | |
| --- | --- | --- | --- |
| | | 17-1 | 17-2 |
| Temp.(°C.) | — | 351 | 401 |
| Pressure (atm) | — | 10.0 | 10.0 |
| H$_2$ Feed Rate (cc/min) | — | 50 | 50 |
| HC Feed Rate (g/hr) | — | 0.02 | 0.02 |
| H$_2$/HC inlet | — | 625 | 625 |
| WHSV (g/g/hr)* | — | 0.02 | 0.02 |
| Analysis (wt. %) | | | |
| methylcyclohexane | 99.69 | 43.55 | 9.77 |
| toluene | 0.31 | 8.11 | 52.26 |
| Other C$_7$ | — | 42.80 | 25.09 |
| xylenes | — | — | 0.68 |
| benzene | — | 0.15 | 2.00 |
| Other C$_2$-C$_6$ | — | 0.15 | 3.45 |

TABLE XVII-continued

Tungsten Cobalt Eta Phase Catalyst

| | Run Number | | |
|---|---|---|---|
| | feed | 17-1 | 17-2 |
| $CH_4$ | — | 5.23 | 6.74 |

*weight hourly space velocity

In these specific examples, for equilibration at constant carbon activity, the following reaction may be employed:

$$2(CO)(g) \: CO_2(g) + C(s) \tag{I}$$

where the CO and $CO_2$ are gas phase species and C(s) is the solid carbon phase available for reaction to form the desired carbide phase, dissolved carbon or free carbon. From equation (I) the equilibrium carbon activity ($a_c$) of a $CO/CO_2$ gas mixture is

$$a_c = \frac{p^2_{CO}}{p_{CO2}} \exp(-G°_I/RT) \tag{II}$$

where $G°_I$ is the standard free energy of formation of 1 mole of carbon in reaction I above at the reaction temperature T, molar gas constant R. For a fixed total reactive gas pressure and ratio of the partial pressure of CO ($p_{CO}$) to the partial pressure of $CO_2$ ($p_{CO2}$) $p_{CO}/p_{CO2}$ the equilibrium carbon activity of the gas environment is fixed by equation (II). Two issues are considered in fixing the carbon activity with $CO/CO_2$ gas mixtures for the method of the invention: control of carbon activity should be easy and accurate and the equilibrium oxygen activity of the $CO/CO_2$ mixture used should be below that for which any oxide phase is stable at the reaction temperature. The equilibrium oxygen activity of a $CO/CO_2$ gas mixture can be calculated from the reaction:

$$2CO_2 \: 2CO + O_2 \tag{III}$$

for which the oxygen partial pressure ($p_{O2}$) is given by

$$p_{O2} = \frac{(p_{CO2})}{p_{CO}} \exp\left(-\frac{G°_{III}}{RT}\right) \tag{IV}$$

where $G°_{III}$ is standard free energy of formation of one mole of $O_2$ in equation (III) at the reaction temperature T. Equations (IV) and (II) show that the oxygen partial pressure and carbon activity at constant total reactive gas pressure $P_t$ (where $P_t = p_{CO} + p_{CO2}$) and temperature are coupled. At constant T and $P_t$, measurement of the oxygen partial pressure of the gas phase therefore is a unique determination of the carbon activity of the gas phase. This observation provides a simple and precise method for the determination and control of the carbon activity. The oxygen partial pressure of the gas phase may, for example, be continuously measured by means of a 7½% calcia stabilized zirconia oxygen probe located ideally in the hot zone of the furnace in which the thermodynamic conversion of the reactive precursor is carried out. The carbon activity of the gas phase is then calculated by equation (II) from a knowledge of the total reaction pressure, temperature and $p_{CO}/p_{CO2}$ as determined by equation (IV). Generally, the coupling of equations I and III requires that the total pressure in the system be adjusted so that no undesirable oxide phase is stable at conditions required to form the desired carbide phase.

What is claimed is:

1. An eta phase composition in powder form, prepared in the absence of sulfur or sulfur bearing compounds, said powder having a surface area greater than about $2m^2/g$ and said eta phase consisting essentially of $X_6Y_6Z_a$, which comprises carbides, nitrides, or carbonitrides wherein X is at least one element selected from the group consisting of Mo and W, Y is at least one element selected from the group consisting of Fe, Co, Ni, Mo and W, Z is at least one element selected from the group consisting of C, N and combinations thereof such that when Z is N, a is greater than or equal to 1 but less than or equal to 2 and when Z is C, a is greater than 1 but less than or equal to 2 except when Z is C and Y is Fe, then a is greater than or equal to 1 but less than or equal to 2.

2. The eta phase of claim 1 wherein said phase comprises an eta phase carbide where a is greater than 1 but less than or equal to 2.

3. The eta phase of claim 1 wherein said phase comprises and eta phase nitride.

4. The eta phase of claim 1 wherein said phase comprises an eta phase carbonitride.

5. An eta phase in powder form, prepared in the absence of sulfur or sulfur bearing compounds which comprises carbides, nitrates or carbonitrides said powder having a surface area greater than about $2m^2/g$ and said phase being at least one eta-phase composition selected from the group consisting of:
$Mo_6Fe_6Z_a$, $Mo_6Co_6Z_a$, $Mo_6Ni_6Z_a$,
$Mo_6(FeCo)_6Z_a$, $Mo_6(FeNi)_6Z_a$, $Mo_6(CoNi)_6Z_a$,
$Mo_6(FeCoNi)_6Z_a$, $W_6Fe_6Z_a$, $W_6Co_6Z_a$,
$W_6Ni_6Z_a$, $W_6(FeCo)_6Z_a$, $W_6(FeNi)_6Z_a$,
$W_6(Co,Ni)_6Z_a$, $W(Fe,Co,Ni)_6Z_a$, $(W,Mo)_6Fe_6Z_a$,
$(W,Mo)_6Co_6Z_a$, $(W,Mo)_6Ni_6Z_a$,
$(W,Mo)_6(Fe,Co)_6Z_a$,
$(W,Mo)_6(Fe,Ni)_6Z_a$, $(W,Mo)_6(Co, Ni)_6Z_a$,
$(W,Mo)_6(Fe,Co,Ni)_6Z_a$,
wherein Z is at least one element selected from the group consisting of C, N and combinations thereof such that when Z is N, a is greater than or equal to 1 but less than or equal to 2 and when Z is C, a is greater than 1 but less than or equal to 2 except when Z is C and Y is Fe, then a is greater than or equal to 1 but less than or equal to 2.

6. A method for producing an eta phase carbide, nitride or carbonitride composition, said method comprising providing a precursor compound, said precursor compound including at least two eta phase forming metals, and a ligand containing carbon, nitrogen or combinations thereof, thermally decomposing said precursor compound in a nonoxidizing atmosphere that is free of sulfur or sulfur bearing compounds and reacting said carbon, nitrogen or combinations thereof derived from decomposition of said ligand with said metals to form said eta phase.

7. The method of claim 6 wherein said eta phase forming metals are at least two metals selected from the group consisting of tungsten, molybdenum, nickel, cobalt and iron.

8. The method of claim 6 wherein said eta phase forming metals are molybdenum and nickel.

9. The method of claim 6 wherein said eta phase forming metals are molybdenum and cobalt.

10. The method of claim 6 wherein said eta phase forming metals are molybdenum and iron.

11. The method of claim 6 wherein said eta phase forming metals are tungsten and nickel.

12. The method of claim 6 wherein said eta phase forming metals are tungsten and cobalt.

13. The method of claim 6 wherein said eta phase forming metals are tungsten and iron.

* * * * *